(12) United States Patent
Chattopadhyay et al.

(10) Patent No.: US 8,142,814 B2
(45) Date of Patent: *Mar. 27, 2012

(54) METHOD AND APPARATUS FOR SUPERCRITICAL FLUID ASSISTED PARTICLE PRODUCTION

(75) Inventors: Pratibhash Chattopadhyay, North Royalton, OH (US); Boris Y. Shekunov, Aurora, OH (US); Jeffrey S. Seitzinger, Broadview Heights, OH (US)

(73) Assignee: Ferro Corporation, Cleveland, OH (US)

( * ) Notice: Subject to any disclaimer, the term of this patent is extended or adjusted under 35 U.S.C. 154(b) by 1683 days.

This patent is subject to a terminal disclaimer.

(21) Appl. No.: 10/541,292

(22) PCT Filed: Jan. 30, 2004

(86) PCT No.: PCT/US2004/003575
§ 371 (c)(1),
(2), (4) Date: Feb. 23, 2006

(87) PCT Pub. No.: WO2004/071645
PCT Pub. Date: Aug. 26, 2004

(65) Prior Publication Data
US 2006/0145375 A1    Jul. 6, 2006

Related U.S. Application Data

(60) Provisional application No. 60/445,901, filed on Feb. 7, 2003.

(51) Int. Cl.
*A61K 9/14* (2006.01)

(52) U.S. Cl. ............. 424/489; 424/499; 424/502; 264/5
(58) Field of Classification Search .................. None
See application file for complete search history.

(56) References Cited

U.S. PATENT DOCUMENTS

| | | | | |
|---|---|---|---|---|
| 5,776,486 A | * | 7/1998 | Castor et al. ................. | 424/450 |
| 6,143,321 A | * | 11/2000 | Needham et al. ............. | 424/450 |
| 6,468,506 B1 | * | 10/2002 | Rossling et al. .............. | 424/9.5 |
| 6,998,051 B2 | * | 2/2006 | Chattopadhyay et al. .... | 210/634 |
| 7,083,748 B2 | * | 8/2006 | Chattopadhyay et al. .... | 264/14 |

FOREIGN PATENT DOCUMENTS

WO    WO 9628191 A1 *    9/1996

* cited by examiner

*Primary Examiner* — Carlos Azpuru
*Assistant Examiner* — Casey Hagopian
(74) *Attorney, Agent, or Firm* — Rankin, Hill & Clark LLP

(57) ABSTRACT

The present invention provides an apparatus and methods of producing particles that include a polymer, a wax and/or lipid and, optionally, a biologically active substance. In accordance with the methods of the invention, a load stock including a polymer, a wax and/or a lipid that is a solid at standard temperature and pressure and, optionally, a biologically active substance is provided. The load stock is contacted with a supercritical fluid to form a melt. The melt is contacted with a polar solvent under suitable conditions to form an emulsion. The emulsion is expanded across a pressure drop to form solid particles that include the load stock. The methods and apparatus facilitate the production of very small particles that have a narrow particle size distribution.

8 Claims, 4 Drawing Sheets

METHOD AND APPARATUS FOR SUPERCRITICAL FLUID ASSISTED PARTICLE PRODUCTION

BACKGROUND OF THE INVENTION

1. Field of Invention

The present invention relates generally to an apparatus and methods for producing particles that include a polymer, a wax and/or a lipid and, optionally, a biologically active substance.

2. Description of Related Art

Several processing techniques utilize the enhanced mass-transfer properties and benign nature of supercritical fluids or near-critical fluids or compressed gases (hereinafter collectively referred to as "supercritical fluids") to produce composite or single-material particles. One of the conventional supercritical fluid processing techniques, which is sometimes referred to as the Particles from Gas-Saturated Solutions ("PGSS") processing technique, uses a supercritical fluid to melt a solid material into a fluid or semi-fluid mass that can be sprayed into a collection vessel. The term "melt" as used in this context denotes that the supercritical fluid reduces the viscosity of the solid material (e.g., via plasticization, swelling or dissolution) so as to render it fluid or semi-fluid, which can be further processed as such. In other words, the formerly solid material can be flowed, pumped or sprayed as a fluid or semi-fluid.

The conventional PGSS particle production method exploits this characteristic by flowing the melt through a nozzle across a pressure drop into an expansion chamber that is maintained at a lower pressure than the vessel containing the melt. When the melt is sprayed through the nozzle into the expansion chamber, the supercritical fluid decompresses and rapidly expands into a gas. This causes the melt to undergo three significant changes that transform the melt into solid particles. First, as supercritical fluid expands from the melt, the remaining supercritical fluid loses its solvating power and the melt returns to a solid state. Second, the rapid expansion of the supercritical fluid into a gas results in a significant reduction in the temperature of the melt, which also assists in returning the melt to a solid phase. Third, the expansion of the supercritical fluid to a gas fractures the melt into small particles that solidify in the form of particles.

While the conventional PGSS process provides a method of forming particles at mild operating temperatures without using any potentially destructive solvents, it does suffer from several disadvantages. For example, it is very difficult to obtain particles in the low micron particle size range that have a relatively narrow particle size distribution using the conventional PGSS process. Certain biologically active materials, especially those materials that do not form a melt upon contact with supercritical fluid at mild operating conditions, simply cannot be processed using the conventional PGSS process into small particles.

Another problem with the conventional PGSS process is that it tends to form agglomerated particles, which is believed to occur as the result of the formation of bridges between particles during expansion. Moreover, the particles formed according to the conventional PGSS process tend to be irregular in shape.

Keeping the above-mentioned limitations of the conventional PGSS process in mind, it would be highly desirable to have a method for producing particles that provides the benefits of conventional PGSS processing but does not suffer from the limitations of conventional PGSS processing. Such a process would preferably produce particles having a narrow particle size distribution. Moreover, the process should also provide for enhanced control over the size and morphology of the particles produced.

BRIEF SUMMARY OF THE INVENTION

The present invention provides an apparatus and methods for producing particles that include a polymer, a wax and/or lipid and, optionally, a biologically active substance. In accordance with the methods of the invention, a load stock comprising a polymer, a wax and/or a lipid that is a solid at standard temperature and pressure and, optionally, a biologically active substance is charged with a supercritical fluid to form a melt. The melt is then contacted with a polar solvent that further preferably comprises a suitable surfactant, under mixing conditions, to form an emulsion. The emulsion is then expanded across a pressure drop to form solid particles that include the load stock. In one embodiment of the invention, the emulsion includes a discontinuous phase that includes the melt and a continuous phase that includes the polar solvent. In another embodiment of the invention, the emulsion includes a discontinuous phase that includes the polar solvent and a continuous phase that includes the melt.

Unlike the conventional PGSS process, which involves expanding a melt rather than an emulsion across a pressure drop to form solid particles, the present methods provide for substantially greater control over factors such as particle size, particle size distribution, and particle morphology. Furthermore, the methods according to the invention make it possible to produce very small particles from materials that cannot be formed into small particles using the conventional PGSS process.

The foregoing and other features of the invention are hereinafter more fully described and particularly pointed out in the claims, the following description setting forth in detail certain illustrative embodiments of the invention, these being indicative, however, of but a few of the various ways in which the principles of the present invention may be employed.

DETAILED DESCRIPTION OF THE INVENTION

Figure 1:
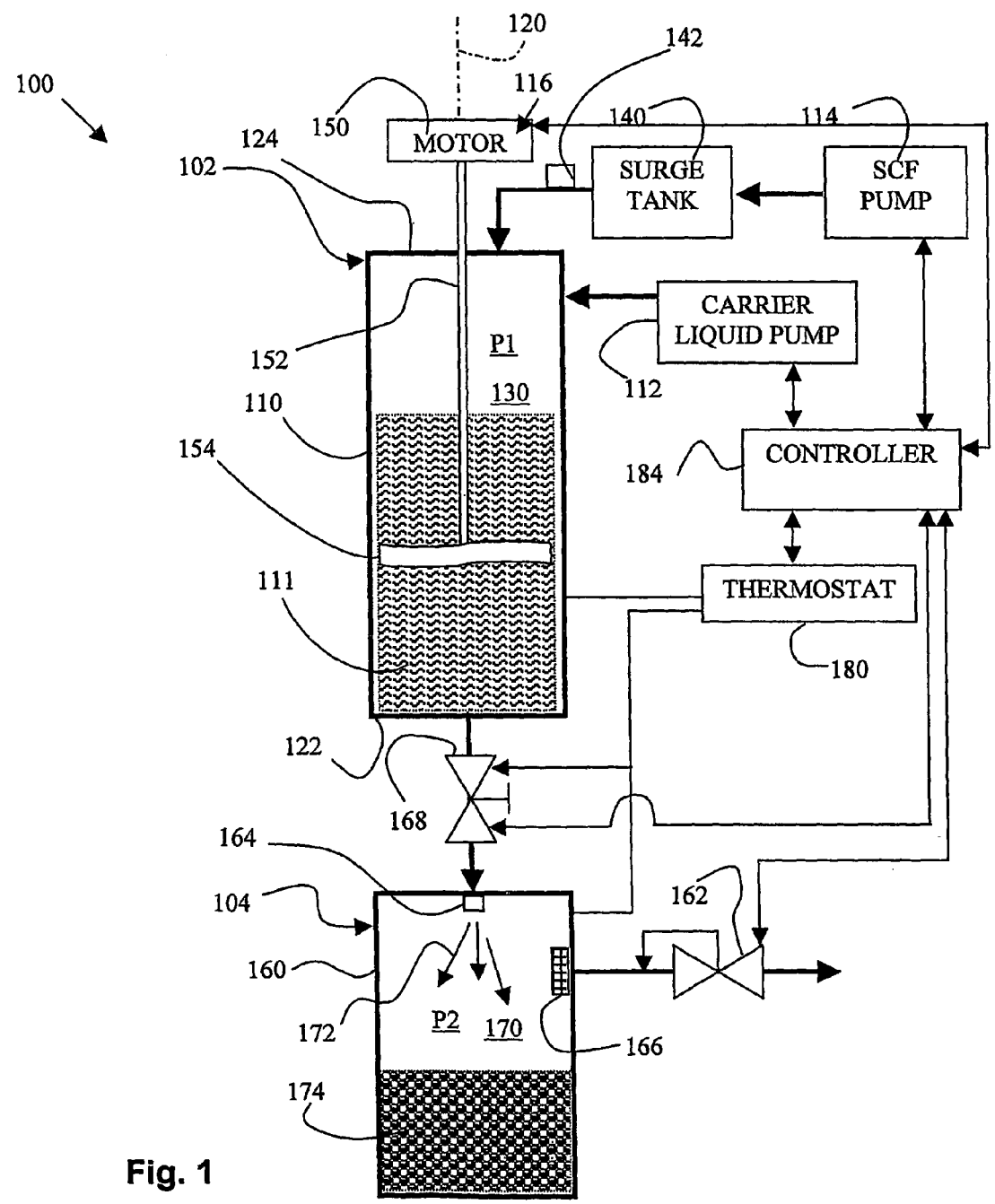
FIG. 1 is a schematic drawing of an apparatus for implementing a method according to the invention.

An exemplary apparatus 100 for implementing the methods according to the invention is shown in FIG. 1. The apparatus 100 includes an emulsification and mixing apparatus 102 and an expansion apparatus 104. The emulsification apparatus 102 includes an emulsification vessel 110, a polar solvent pump 112, a supercritical fluid pump 114, and an emulsification assembly 116.

The emulsification vessel 110 is preferably tubular and defines an axis 120, and has first and second ends 122, 124 that are spaced axially apart. Preferably, the axis 120 is oriented vertically such that the first end 122 is below the second end 124. That is, the second end 124 is UP and the first end 122 is DOWN when moving along the axis 120. The emulsification vessel 110 has an inner surface that defines an emulsification chamber 130. The pressure in the emulsification chamber 130 is denoted with the reference number P1. The mixing apparatus 102 includes means for accessing the interior of the emulsification vessel 110 so as to charge the interior with a load stock.

The load stock comprises a polymer, a wax and/or a lipid that is a solid at standard temperature and pressure. Throughout the instant specification and in the appended claims, the phrase "standard temperature and pressure" means 25° C. and 1 atmosphere pressure. Suitable polymers for use in the invention include, for example, polysaccharides, polyesters, polyethers, polyanhydrides, polyglycolides (PLGA), polylactic acid (PLA), polycaprolactone (PCL), polyethylene glycol (PEG) and polypeptides. Suitable lipids include, for example, glycerides.

The load stock can further optionally comprise a biologically active substance such as, for example, a drug, a pharmaceutical, or a therapeutic agent. In the preferred embodiments of the invention, the load stock does comprise a biologically active substance, which is incorporated with the polymer, wax and/or lip in a desired manner to form a coated, encapsulated or taste-masked formulation, or a controlled prolonged or sustained release formulation. It will be appreciated that the load stock can also further comprise other substances such as, for example, pigments, sugars, diagnostic aids and/or markers, nutritional materials, proteins, peptides, animal and/or plant extracts, dyes, antigens, catalysts, nucleic acids and combinations thereof.

The load stock must be capable of forming a melt 111 when contacted with a supercritical fluid under pressure. Throughout the instant specification and in the appended claims, the term "melt" denotes that the supercritical fluid reduces the viscosity of the load stock (e.g., via plasticization, swelling or dissolution) so as to render it a fluid or semi-fluid that can be processed as such. In other words, the load stock can be flowed, pumped or sprayed as a fluid or semi-fluid. In addition, the melt 111 must be generally insoluble in the polar solvent selected for use in the invention, at least insofar as is necessary to form an emulsion.

The polar solvent pump 112 is preferably a high-pressure liquid chromatography (HPLC) reciprocating pump such as the model PU-2080, which is commercially available from Jasco Inc. (Easton, Md.). Suitable alternative pumps include syringe type pumps, such as the 1000D or 260D pumps, which are commercially available from Isco Inc. (Lincoln, Nebr.). The polar solvent pump 112 is in fluid communication with the emulsification chamber 130 via a liquid inlet nozzle that extends though a sidewall of the emulsification vessel 110.

The supercritical fluid pump 114 is preferably a P-200 high-pressure reciprocating pump commercially available from Thar Technologies, Inc. (Pittsburgh, Pa.). Suitable alternative pumps include diaphragm pumps and air-actuated pumps that provide a continuous flow of supercritical fluid. The supercritical fluid pump 114 supplies supercritical fluid into a surge tank 140 and a metering valve 142 so as produce a pulse-free flow. The supercritical fluid pump 114 is in fluid communication with the emulsification chamber 130, and thus supplies supercritical fluid through the surge tank 140 and into the chamber 130. As used herein, "supercritical fluid" includes fluids in supercritical and near-critical states, as well as compressed and liquefied gases.

The emulsification assembly 116 includes a motor 150, a shaft 152 extending from the motor 150 through the second end 116 of the emulsification vessel 110 and into the chamber 130, and a rotor 154 disposed at a distal end of the shaft 152 and located in the chamber 130. The mixing rate is controlled by the rotation speed and geometry (type and diameter) of the rotor 154. In this embodiment, the rotor 154 is a propeller shaped two-bladed emulsifier device. Additional, supplemental and alternative shearing methods include both static and moving emulsification devices, such as baffles, rotors, turbines, shear-mixers, homogenizers or microfluidizers, ultrasonic devices, and other devices or mechanisms used to emulsify or homogenize the contents of the emulsification apparatus 102.

With reference to the expansion apparatus 104, the expansion apparatus 104 includes a receiving or expansion vessel 160, a backpressure regulator 162, a nozzle 164, and a filter 166. The expansion vessel 160 is in fluid communication with the emulsification vessel 110 via a release valve 168, which is disposed between the emulsification vessel 110 and the expansion vessel 160, and is attached to the nozzle 164. The filter 166 is adjacent an outlet from the expansion vessel 160 to the backpressure regulator 162.

The expansion vessel 160 is preferably tubular, and has an inner surface that defines an expansion chamber 170. The pressure inside the expansion chamber is denoted with reference number P2. The expansion vessel 160 preferably has means, not shown, to access the expansion chamber 170 so as to remove the contents subsequent to an expansion operation.

The backpressure regulator 162 is preferably a 26-1700-type regulator, which is commercially available from Tescom, USA (Elk River, Minn.). The backpressure regulator 162 maintains the pressure P2 in the expansion chamber 170 in a predetermined range of pressures. The release valve 168 is preferably a standard commercially available valve and is interchangeable with other like valves that are known to those of ordinary skill in the art. The release valve 168 controls the rate of flow of the emulsion from the emulsification chamber 130 through the nozzle 164 and into the expansion chamber 170. Accordingly, the release valve 168 and the backpressure regulator 162 cooperate to maintain the desired pressure P2 in the expansion chamber 170 during operation.

A thermostat 180 communicates with heating elements (not shown) that are located proximate to the emulsification vessel 110, the expansion vessel 160, and the release valve 168. A controller 184 communicates with and controls the polar solvent pump 112, the supercritical fluid pump 114, the thermostat 180, the emulsification assembly 116, the backpressure regulator 162, and the relief valve 168. Suitable alternative controllers are interchangeable therewith.

With reference to the polar solvent that the polar solvent pump 112 supplies to the chamber 130, the polar solvent is selected based on its ability to form an emulsion with the melt 111 (i.e., the plasticized load stock). Suitable surfactants can be added to the polar solvent in order to aid in the formation of the emulsion. Accordingly, the relative solubility of the substances in the load stock must be compared to the possible polar solvents. In some instances, some solubility of the load stock in the polar solvent may be desired. In addition, the polar solvent can have some solubility in the supercritical fluid. Sufficient polar solvent remains undissolved in the supercritical fluid, and undissolved with the load stock so as to form an emulsion with the melt 111. The emulsion, or reverse emulsion depending on the relative quantities of the materials used, reduces the viscosity of the melt 111.

Preferred polar solvents include water and polar alcohols. The most preferred polar solvent is water. Other materials can be added to the polar solvent to form a solution, an emulsion, a suspension or a mixture. If additional materials are dissolved, suspended or dispersed in the polar solvent, the resultant solid particles can contain both the constituents of the melt as well as the additional materials carried by the polar solvent. Alternatively, the additional materials mixed with the polar solvent can be washed or carried away from the particles by a subsequent separation of the polar solvent from the solid particles.

Surfactants or modifiers can be added to the polar solvent and/or the melt, as desired, so as to affect properties of the emulsion. The affected properties can include, for example, the rheology, the atomization, the particle stability properties, and/or the interaction of the supercritical fluid with the load stock or polar solvent.

With reference to the supercritical fluid that the supercritical fluid pump 114 supplies to the chamber 130, the supercritical fluid is preferably supercritical carbon dioxide ("$CO_2$"). Suitable alternative supercritical fluids include water, nitrous oxide, dimethylether, straight chain or branched C1-C6-alkanes, alkenes, alcohols, and combinations thereof. Preferable alkanes and alcohols include ethane, ethanol, propane, propanol, butane, butanol, isopropane, isopropanol, and the like. The supercritical fluid is chosen generally with reference to the ability of the supercritical fluid to melt, plasticize or swell the load stock during operation.

The supercritical fluid contacts the load stock and forms the melt and the polar solvent contacts the melt and forms an emulsion. It will be appreciated that materials that are partially soluble in each other may form emulsions under proper conditions, and are thus such materials may also be suitable for use with the present invention.

Figure 2:
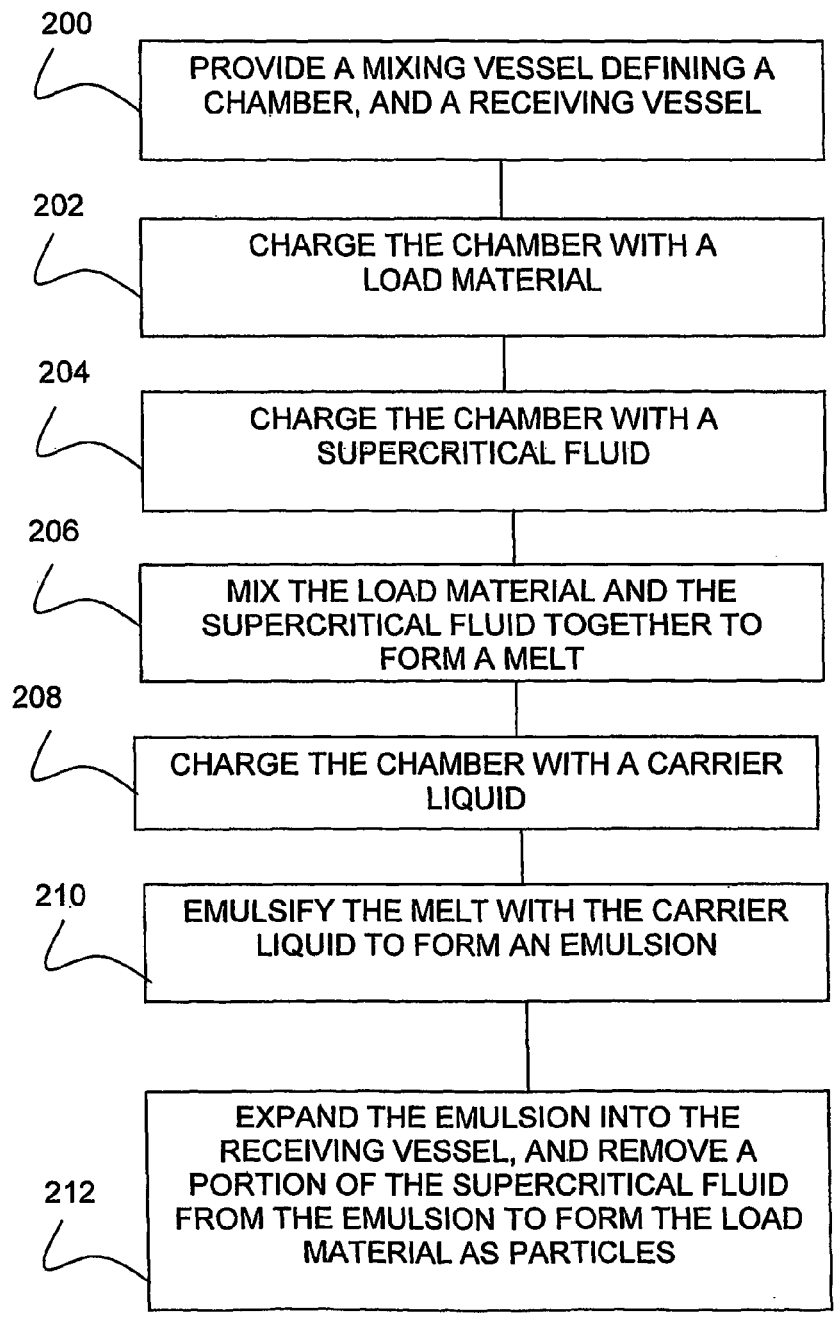
FIG. 2 is a block diagram of a method according to the invention.

During operation of the apparatus 100 (step 200) and with reference to FIG. 2, the emulsification vessel 110 is charged with a quantity of the load stock (step 202). The emulsification vessel 110 is closed and sealed. The controller 184 activates the supercritical fluid pump 114 to supply a quantity of supercritical fluid through the surge tank 140, through the metering valve 142, and into the emulsification chamber 130 (step 204). The supercritical fluid pump 114 increases the pressure P1 in the emulsification chamber 130 to be in a predetermined range of pressures.

The supercritical fluid contacts the load stock. The supercritical fluid acts on the load stock to form the melt 111 (step 206). The controller 180 controls the emulsification assembly 116 to engage the motor 150 so as to rotate the shaft 152 and the rotor 154.

The thermostat 180 and the supercritical fluid pump 114 cooperate to maintain the temperature and the pressure P1 in a generally constant operating range. The temperature and the pressure P1 are maintained about constant. Accordingly, the pressure P1 is generally in a range that has an increased pressure relative to atmospheric pressure.

In this particular embodiment, the controller 184 controls the polar solvent pump 112 to supply the polar solvent into the emulsification chamber 130 (step 208). Alternatively, the polar solvent can be added together with the load stock so as to be present during the formation of the melt. The rotor 154 spins to emulsify the melt 111 with the polar solvent to form an emulsion (step 210). In one embodiment of the invention, the discontinuous phase of the emulsion comprises the melt and the continuous phase of the emulsion comprises the polar solvent. In another embodiment of the invention, the discontinuous phase of the emulsion comprises the polar solvent and the continuous phase comprises the melt.

The pressure P2 in the expansion vessel 160 is preferably maintained at about atmospheric pressure. Optionally, the pressure P2 can be controlled by the backpressure regulator 162 to be increased relative to atmospheric pressure, and to reduce the difference between the pressures P1, P2 in the vessels 110, 160.

The release valve 168 opens and the emulsion, under the influence of the pressure difference between the chambers 130, 170, flows through the release valve 168 and further though the nozzle 164. The pressurized emulsion is sprayed from the nozzle 164 as indicated by the directional arrows 172 into the chamber 170 (step 212). Because of the pressure drop of the emulsion during spraying (from P1 to the relatively lower pressure P2), the supercritical fluid contained therein flashes from a liquid or compressed state to a gaseous or relatively uncompressed state. The loss of the supercritical fluid from the emulsion increases the melt point and/or glass transition temperature of the load stock.

Further, the phase change of the supercritical fluid from liquid to gas reduces the localized temperature of emulsion adjacent to the expansion location (i.e., the nozzle outlet). If a nozzle heater is present, the nozzle can be heated to reduce the level of polar solvent in the particles 174, and to affect particle characteristics, such as size and morphology.

As the melt solidifies or precipitates from the emulsion into a plurality of particles 174, any dissolved or suspended materials, if present, precipitate at substantially the same time. The particles 174 can thus be in the form of composite particles, homogenous or single component materials and crystals or, alternatively, microspheres or microcapsules or the like. Rather than discrete particles, the expanded material can also be precipitated as a suspension, a foam or a gel. Further, the particles can have different surface profiles or morphologies, and can be discrete or can be grouped or agglomerated.

If the polar solvent is not removed during the expansion step, the particles 174 may be obtained as a suspension in the polar solvent. For example, if the continuous phase of the emulsion comprises water, and the melt comprises a water-insoluble polymer, wax and/or lipid and a water-insoluble biologically active substance, the resulting solid particles formed by expanding the emulsion may comprise an aqueous suspension of composite solid polymer, wax and/or lipid/biologically active substance particles. The suspension can be subsequently processed to separate the solid particles 174 from the polar solvent. The particles can be washed and filtered to remove surfactants and other material residues. An additional processing step can be implemented such as spray-drying or freeze-drying, by which the polar solvent can be removed from the suspension. A parallel spray-drying can be implemented simultaneously with the expansion by heating the expansion vessel or by supplying a stream of inert heating gas or air in the expansion vessel. A parallel freeze-drying can be implemented simultaneously with the expansion vessel by attaching a vacuum device to the collection vessel and keeping the temperature within this vessel at or below the freezing temperature of the polar solvent.

The following examples are intended only to illustrate the invention and should not be construed as imposing limitations upon the claims. Unless specified otherwise, all ingredients are commercially available from such common chemical suppliers as Sigma Aldrich, Inc. (St. Louis, Mo.) and/or Fisher Scientific International, Inc. (Hanover Park, Ill.).

EXAMPLE 1

Preparation.

Initially, 6 grams (g) of tripalmitin (a lipid, model compound) was charged to an emulsification vessel. The emulsification vessel was closed and pressurized with carbon dioxide gas ($CO_2$) to an operating pressure of 300 bar.

The thermostat was set at a predetermined temperature, and the temperature was ramped to 318 Kelvin (K). The thermostat monitored and maintained the temperature at a constant temperature of 318 K. At the predetermined temperature and pressure, the carbon dioxide became supercritical. The controller was set to maintain the emulsifier device to rotate the emulsifier blade at a constant agitation speed of 4000 revolutions per minute (rpm).

The tripalmitin and $CO_2$ mixture was allowed to equilibrate and mix at 4000 rpm for one hour (hr).

A solution pump was activated and pumped an aqueous solution of TWEEN-80 (1% w/w) into the emulsification vessel. The agitation speed of 4000 rpm was maintained during the addition of the aqueous phase. The aqueous solution of TWEEN-80, the tripalmitin and the supercritical carbon dioxide formed an emulsion.

Expansion of Particles.

A release valve was opened to communicate the emulsion from the emulsification vessel to an expansion vessel. Specifically, the release valve communicated the emulsion to a nozzle that opened into the interior of the expansion vessel. The nozzle was a multiple nozzle plate defining ten orifices, each orifice had a diameter of 180 micrometers (μm). The pressure in the interior of the expansion vessel was standard atmospheric pressure, and the pressure in the emulsification vessel was adjusted to remain at a constant 30 megapascals (MPa).

The supercritical fluid flashed into a gas at atmospheric pressure. The particles were obtained in the form of concentrated liquid suspension of particles in the aqueous solution of TWEEN-80.

Analysis of the Particles.

Figure 3:
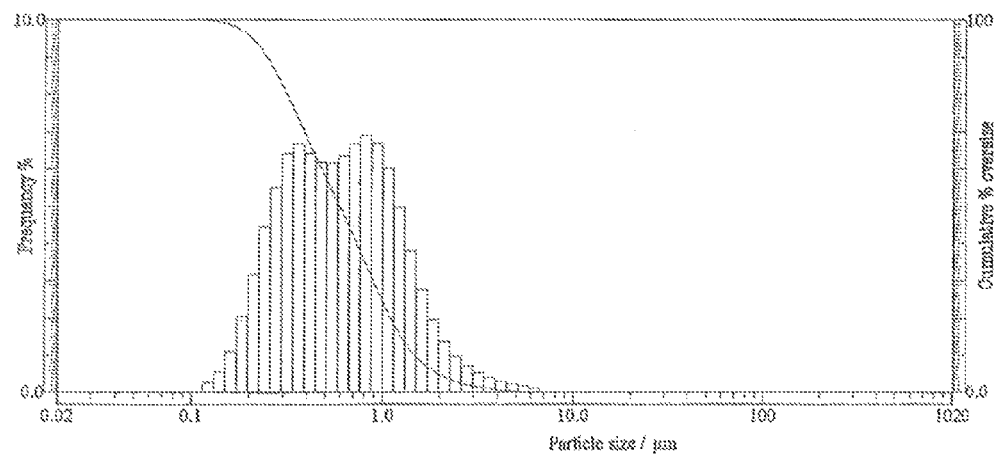
FIG. 3 is graph showing the particle size distribution of particles formed in accordance with Example 1.

Analysis of the particles was performed using a Scanning Electron Microscope (SEM) to determine size and morphology, using a laser diffraction particle analyzer to determine the particle size distribution in suspension, and using a Differential Scanning Calorimeter (DSC) to determine polymorphism and melting behavior of dried particles. The particles produced in Example 1 were compared against particles prepared by a conventional PGSS process using the same materials (i.e., no aqueous solution was pumped into the melt to form an emulsion). The particles obtained from the two processes had different morphologies. There were more platelets in the particles of Example 1 compared to the acicular shapes formed by the conventional method. The particles produced in Example 1 were sub-micron in size, and were less aggregated relative to the conventionally produced particles. In particular, the particles of Example 1 had a volume mean diameter that was 786 nanometers (nm). FIG. 3 is graph showing the particle size distribution of particles formed in accordance with Example 1.

EXAMPLE 2

Preparation.

Initially 6 grams of tripalmitin was charged into the emulsification vessel, and 0.6 grams of ketoprofen were also charged into the emulsification vessel. The emulsification vessel was pressurized with $CO_2$ to the operating pressure 300 bar. The thermostat maintained the emulsification vessel at a constant temperature of 328 K. At the predetermined temperature and pressure, the carbon dioxide became supercritical. The controller was set to maintain the emulsifier device to rotate the emulsifier blade at a constant agitation speed of 4250 revolutions per minute (rpm).

The ketoprofen and the tripalmitin dissolved in the supercritical carbon dioxide. The molten solution or melt was mixed and allowed to equilibrate for one hour. A solution pump was activated and pumped an aqueous solution of TWEEN-80 (2.5% w/w) into the emulsification vessel. The agitation speed of 4250 rpm was maintained during the addition of the aqueous phase. The aqueous solution of TWEEN-80, the tripalmitin, the ketoprofen and the supercritical carbon dioxide formed an emulsion.

Expansion of Particles.

A release valve was opened to communicate the emulsion from the emulsification vessel to an expansion vessel. Specifically, the release valve communicated the emulsion to a nozzle that opened into the interior of the expansion vessel. The nozzle was a multiple nozzle plate defining ten orifices; each orifice had a diameter of 180 micrometers (mm). The pressure in the interior of the expansion vessel was standard atmospheric pressure, and the pressure in the emulsification vessel was adjusted to remain at a constant 300 bar. The supercritical fluid flashed into a gas at atmospheric pressure. The particles were obtained in the form of concentrated liquid suspension of particle in the aqueous solution of TWEEN-80.

Analysis of the Particles.

Figure 4:
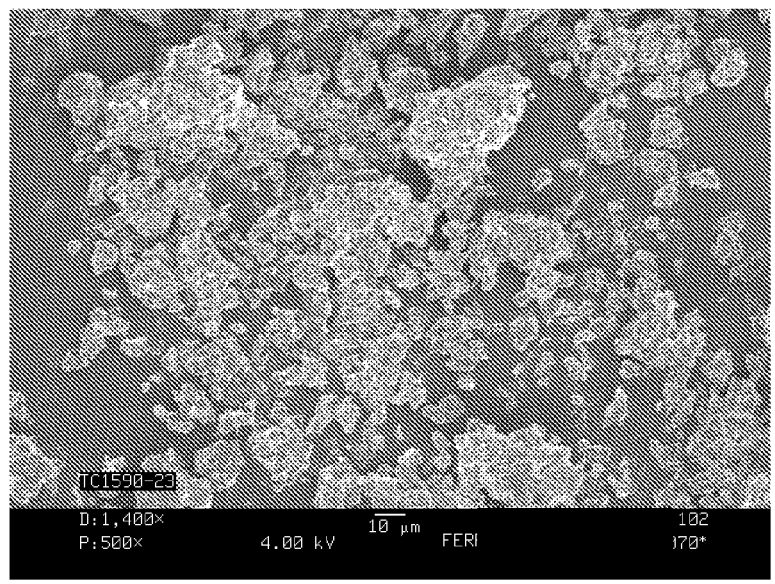
FIG. 4 is Scanning Electron Micrograph (SEM) of tripalmitin encapsulated Ketoprofen particles formed in Example 2.
Figure 5:
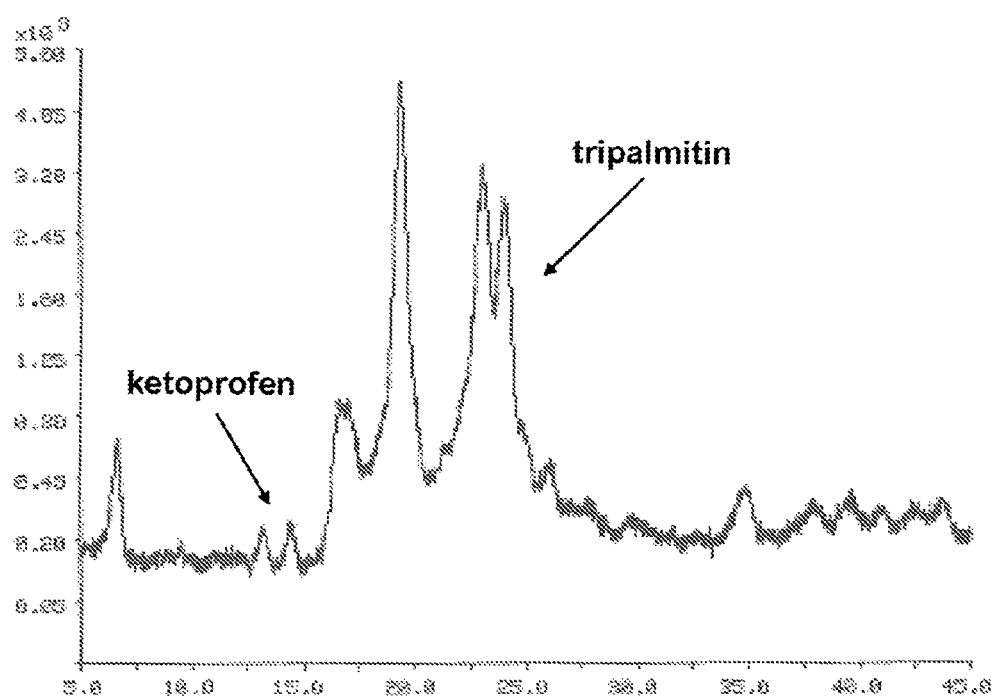
FIG. 5 is an X-ray Diffraction (XRD) plot of the tripalmitin encapsulated Ketoprofen particles formed in Example 2.

Analysis of the particles formed in Example 2 was performed using a Scanning Electron Microscope (SEM) to determine size and morphology, using a laser diffraction particle analyzer to determine particle size distribution in the suspension, and using X-ray powder diffraction (XRPD) to determine crystallinity and drug content. The particles consisted of non-aggregated composite particles. The particles had a volume mean diameter of about 12-20 microns, as shown in FIG. 4. The chemical composition of the particles was about 9% w/w of ketoprofen. The ketoprofen was present in the form sub-micron sized crystalline particles embedded into or coated onto the tripalmitin, as shown in FIG. 5.

Additional advantages and modifications will readily occur to those skilled in the art. Therefore, the invention in its broader aspects is not limited to the specific details and illustrative examples shown and described herein. Accordingly, various modifications may be made without departing from the spirit or scope of the general inventive concept as defined by the appended claims and their equivalents.

What is claimed is:

1. A method of producing solid particles comprising the steps of:
    providing a load stock comprising:
        at least one material that is a solid at standard temperature and pressure selected from the group consisting of polysaccharides, polyesters, polyethers, polyanhydrides, polyglycolide, polylactic acid, polycaprolactone, polyethylene glycol, polypeptides, waxes and glycerides; and
        optionally, a biologically active substance;
    contacting the load stock with a supercritical fluid to form a melt;
    contacting the melt with a polar solvent to form an emulsion, the emulsion having a discontinuous phase comprising the melt and a continuous phase comprising the polar solvent; and
    expanding the emulsion across a pressure drop to form solid particles comprising the load stock.

2. The method according to claim 1 wherein the emulsion is expanded through a heated nozzle.

3. The method according to claim 1 wherein the solid particles are collected in an expansion vessel.

4. The method according to claim 3 wherein a stream of inert gas flows through the expansion vessel to remove the expanded supercritical fluid.

5. The method according to claim 1 further comprising adjusting a rate of expansion of the emulsion across the pressure drop to control the morphology and/or size of the solid particles.

6. The method according to claim 1 wherein the supercritical fluid is carbon dioxide.

7. The method according to claim 1 wherein the polar solvent is selected from the group consisting of water and alcohol.

8. The method according to claim 1 wherein a surfactant is added to the polar solvent before the polar solvent is contacted with the melt.

* * * * *